United States Patent [19]
Mann et al.

[11] Patent Number: 5,573,003
[45] Date of Patent: Nov. 12, 1996

[54] LOW-POWER DELTA MODULATOR FOR INTRACARDIAL SIGNAL MONITORING IN A CARDIAC DEVICE

[75] Inventors: Brian M. Mann, Beverly Hills; Min-Yaug Yang, Monterey Park, both of Calif.

[73] Assignee: Pacesetter, Inc., Sylmar, Calif.

[21] Appl. No.: 379,067

[22] Filed: Jan. 27, 1995

[51] Int. Cl.⁶ ............................................. A61B 5/0402
[52] U.S. Cl. .......................... 128/696; 607/16; 341/164
[58] Field of Search ............................ 341/164; 128/696, 128/710; 607/16, 27; 364/413.06

[56] References Cited

U.S. PATENT DOCUMENTS

| | | | |
|---|---|---|---|
| 3,228,025 | 1/1966 | Welch | 340/347 |
| 3,495,073 | 2/1970 | James | 235/92 |
| 3,795,900 | 3/1974 | Monford, Jr. | 340/347 |
| 3,868,679 | 2/1975 | Arneson | 340/347 |
| 4,031,532 | 6/1977 | First | 340/347 |
| 4,097,860 | 6/1978 | Araseki et al. | 340/347 |
| 4,509,529 | 4/1985 | Money et al. | 128/708 |
| 4,528,549 | 7/1985 | Simpson | 340/347 |
| 4,573,037 | 2/1986 | Robinton et al. | 340/347 |
| 4,768,018 | 8/1988 | Noujaim | 340/347 |
| 4,940,982 | 7/1990 | Gulczynski | 341/164 |
| 5,014,284 | 5/1991 | Langer et al. | 128/696 |
| 5,022,395 | 6/1991 | Russie | 607/16 |
| 5,084,704 | 1/1992 | Parrish | 341/164 |
| 5,373,292 | 12/1994 | Yasuda | 341/164 |
| 5,458,122 | 10/1995 | Hethuin | 128/696 |

FOREIGN PATENT DOCUMENTS

5683127   7/1981   Japan .

*Primary Examiner*—William E. Kamm
*Assistant Examiner*—Kennedy J. Schaetzle
*Attorney, Agent, or Firm*—Lisa P. Weinberg

[57] ABSTRACT

A low-power delta modulator analog-to-digital converter is provided that is suitable for use in a cardiac stimulating device for monitoring intracardial signals. The delta modulator consumes less power than previously available delta modulators because portions of the delta modulator circuitry are shut down when the signal to be digitized is not rapidly varying. The device uses slow clock pulses for sampling the input signal and subsequently digitizes the sampled signal using a faster clock. After a sampled signal has been digitized, the result is held until the next slow clock pulse. Power consumption is reduced since the delta modulator does not draw substantial amounts of power during this holding period. Further, the output of the delta modulator reflects the magnitude of the change in the analog input, with a separate bit for representing direction. Thus, when the input signal remains constant from one slow clock pulse to the next, the delta modulator does not draw significant power even on that next slow clock pulse.

38 Claims, 4 Drawing Sheets

LOW-POWER DELTA MODULATOR FOR INTRACARDIAL SIGNAL MONITORING IN A CARDIAC DEVICE

BACKGROUND OF THE INVENTION

This invention relates to implantable cardiac devices, such as cardiac stimulating devices and cardiac monitoring devices, particularly to those having analog-to-digital converters of the delta modulator type for monitoring intracardial signals.

Implantable cardiac devices, such as implantable cardiac stimulating devices, are used by individuals who have an irregular heartbeat or are at risk of ventricular fibrillation. For instance, pacemakers can stabilize heart function by electrically stimulating the heart at regular intervals. Defibrillators provide a defibrillating pulse to the heart if necessary. In order to provide access to all modes of pacemaker operation, the heart signal must be accurately measured. This allows proper synchronization between the intrinsic heartbeat and the applied electrical pulses of a pacemaker. Intracardial signal monitoring may also be performed to determine whether defibrillation by the cardiac stimulating device is required.

The intracardial signal generally must be digitized so that a digital processor can be used to implement suitable control algorithms. One type of analog-to-digital converter that is suitable for use in an implantable cardiac device is a delta modulator. When a cardiac device is surgically implanted, an analog-to-digital converter must operate with limited battery power reserves. Indeed, the cardiac device is intended to last a lifetime and replacement entails additional surgery, so minimizing overall power consumption in the device is important. This can be achieved in part by lowering the power use of the analog-to-digital converter.

It would therefore be desirable to be able to provide an implantable cardiac device that has lower power consumption than previously known devices.

It would further be desirable to be able to provide a cardiac device that has a low-power analog-to-digital converter for monitoring intracardial signals.

It would also be desirable to be able to provide a low-power delta modulator for use in a cardiac device for monitoring intracardial signals.

SUMMARY OF THE INVENTION

It is therefore an object of the present invention to provide an implantable cardiac device that has lower power consumption than previously known devices.

It is a further object of the present invention to provide a cardiac device that has a low-power analog-to-digital converter for monitoring intracardial signals.

It is also an object of the present invention to provide a low-power delta modulator for use in a cardiac device for monitoring intracardial signals.

These and other objects of the invention are accomplished in accordance with the principles of the invention by modifying a conventional delta modulator to provide a low-power delta modulator that is more suitable for use in a cardiac stimulating or monitoring device. The delta modulator of the present invention consumes less power than previously available delta modulators because portions of the modulator circuitry are shut down when the signal to be digitized is not rapidly varying.

In accordance with the present invention, a delta modulator for use in a cardiac device is provided for monitoring intracardial signals. The delta modulator has input logic for sampling an analog input signal and providing a sampled input signal, circuitry responsive to control signals for providing a reference voltage, a counter, and control logic for providing the control signals to the circuitry for providing a reference voltage. The circuitry for providing a reference voltage adjusts the reference voltage from an initial reference voltage to substantially equal the sampled input signal in accordance with the control signals. While the circuitry for providing a reference voltage adjusts the reference voltage, the control logic simultaneously causes the counter to count at the rate of a fast clock until the reference voltage has been adjusted to substantially equal the sampled input voltage. The count that is reached is proportional to the voltage difference between the initial reference voltage and the sampled input signal. The control logic further provides a directional signal that is indicative of the direction in which the reference voltage was adjusted. The directional signal and the count are provided as a digital output signal representative of the analog input signal.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

Battery power is a scarce resource in surgically implantable electrical cardiac devices such as pacemakers and cardiac monitoring devices. Therefore, in order to extend battery life or allow the use of smaller batteries, it would be desirable to reduce the power consumption of electronic components of implantable cardiac devices such as analog-to-digital converters, which are used to digitize intracardial electrical signals. Previously, delta modulator analog-to-digital converters have been used that continuously track the intracardial signal. The voltage resolution of these previously known devices depended on the speed of the clock, which was generally operated at frequencies of at least eight KHz to obtain sufficiently accurate measurements.

However, although conventional delta modulators provide access to the digitized signal at each clock cycle, in actuality this data rate would place an excessive burden on other electrical components in a cardiac stimulating device. Therefore, the processors in previously known cardiac devices typically only provide counting every sixteen bits of the digital signal, and use four bits of the counter value to represent the A/D value within these sixteen samples. Therefore, when the clock rate is 8 KHz, the equivalent signal sample rate is 512 Hz. Conventional delta modulators consume power at the same rate during these periods whether the signal is more active or not, because the circuit keeps charging and discharging a capacitor as it oscillates about the signal voltage.

In accordance with the present invention, a low-power delta modulator is provided that has two clocks. The input signal is sampled at a slow clock rate, equivalent to the previous rate at which data was provided to the cardiac stimulating device processor. Between slow clock pulses a fast clock is used to accurately digitize the sampled signal. While the fast clock pulses are counted with a counter, a reference voltage across a capacitor is raised or lowered until it equals the magnitude of the sampled input voltage. At this point the count is held constant until the end of the slow clock cycle. The count, which is proportional to the voltage difference between the sampled input signal and the initial reference voltage, is read out just prior to the next slow clock pulse.

In addition to the count signal, a directional signal is provided that indicates whether the sampled signal is higher or lower than the previous sample. The addition of the directional signal allows the fast clock rate to be cut in half, while still providing the same number of bits of voltage resolution within each slow clock period.

Power is saved using this arrangement because during each slow clock period power is consumed only while the sampled input signal is being digitized. After a signal is digitized, the modulator shuts down for the remainder of the slow clock cycle. Further, power use is substantially reduced during periods when the input voltage is constant, as the signal is digitized quickly and the modulator is therefore "off" for nearly the entire slow clock cycle.

Figure 1:
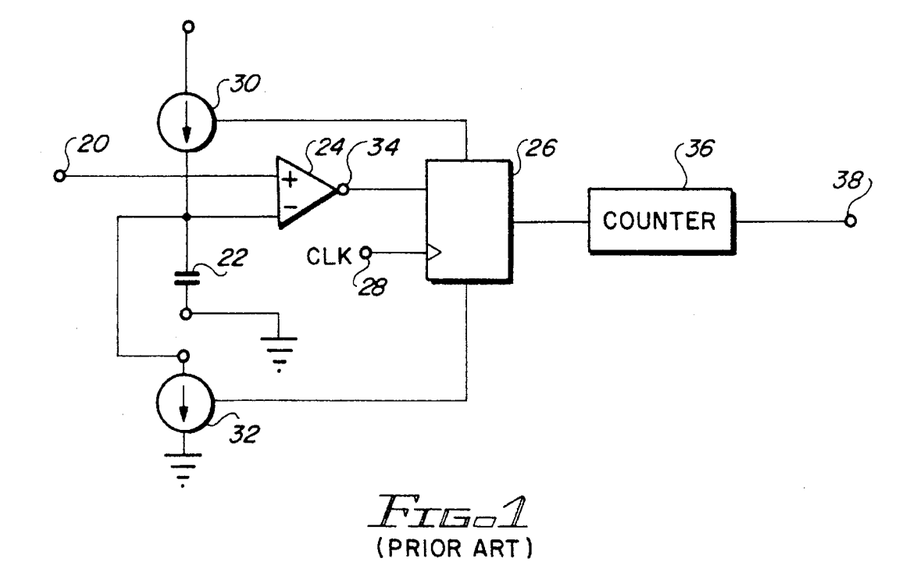
FIG. 1 is a schematic diagram of a conventional analog-to-digital converter of the delta modulator type.

An example of a conventional delta modulator is shown schematically in FIG. 1. In operation, an analog input signal that is applied to input terminal 20 is compared to the voltage of capacitor 22 by comparator 24. The resulting output 34 is fed into control logic 26, which is clocked by a clock signal CLK that is received via clock terminal 28. If the voltage of the analog input signal exceeds the voltage across capacitor 22, output 34 of comparator 24 goes high. In response, control logic 26 enables current source 30 and turns off current source 32, thus charging and increasing the voltage across capacitor 22. While current source 30 is enabled, bidirectional counter 36 counts upward at the rate of the clock signal CLK in accordance with a directional signal received from control logic 26.

Similarly, if the voltage of the analog input signal is less than that of capacitor 22, the output of comparator 24 goes low and the directional signal from control logic 26 causes bidirectional counter 36 to count downward while current source 30 is held off and current source 32 drains capacitor 22. Current sources 30 and 32 are balanced, so that the binary output signal indicative of the count that is provided by bidirectional counter 36 at output terminal 38 is representative of the analog input signal at input terminal 20.

For continuously varying input waveforms, this type of analog to digital converter may perform satisfactorily provided that the clock rate is sufficiently fast to capture rapid fluctuations of the input signal. However, if the signal to be digitized contains relatively long portions with little or no change in voltage, conventional delta modulators such as these are inefficient, because current sources 30 and 32 continuously charge and discharge capacitor 22, even if the input voltage is constant. The resulting excessive power drain is particularly undesirable for use in cardiac stimulating devices, which are surgically implanted in the body and which are intended to operate for a lifetime on the limited power reserves available from a battery that can be changed only through surgery.

Figure 2:
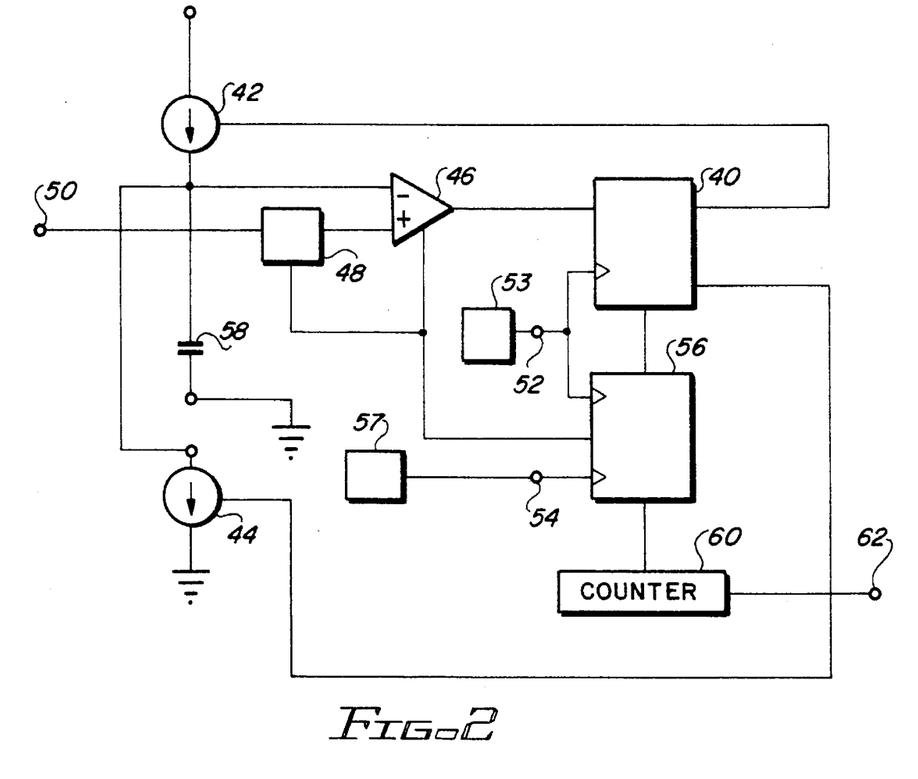
FIG. 2 is a schematic diagram of an illustrative embodiment of a low-power delta modulator in accordance with the present invention.

An illustrative embodiment of a delta modulator suitable for use in a cardiac stimulating device having low-power consumption in accordance with the present invention is shown in FIG. 2. The modulator has a lower power consumption than conventional delta modulators because current supplies 42 and 44, comparator 46, and input amplifier 48 are shut down for a number of clock cycles once the input signal received at input terminal 50 has been digitized. The signal sampling rate is determined by a slow clock signal, preferably with a frequency of 512 Hz, which is applied to clock input terminal 52 by slow clock 53. A faster clock signal, running at a frequency of preferably four KHz (eight times 512 Hz), is applied to clock input terminal 54 of clock logic 56 by fast clock 57.

The speed of fast clock 57 determines how accurately the sampled signal is digitized. With a faster clock, more bits of resolution may be provided during each slow clock cycle. Preferably, the two clocks are synchronized so that there are eight fast clock cycles for each slow clock cycle. Together with a separate measurement of whether the direction of change of the input signal is positive or negative this provides four bits of resolution across the range of anticipated input voltages.

In operation, just prior to a slow clock cycle, input amplifier 48, which is enabled by a signal received from clock logic 56, samples the input signal at input terminal 50. For high accuracy, input logic may include a sample-and-hold circuit. A low-cost alternative would be to use switched capacitor type filtering. Sampling circuitry 48 may be triggered by any suitable control signal that is slightly advanced with respect to the slow clock signal, so that comparator 46, which is also enabled by a signal received from clock logic 56, may compare the sampled input signal to the initial reference voltage across capacitor 58 before the slow clock cycle begins.

When the slow clock signal goes high, the output of comparator 46 is received by control logic 40, which charges capacitor 58 by turning on current source 42 and turning off current source 44 if the sampled input voltage provided to comparator 46 by input amplifier 48 is higher than the voltage across capacitor 58. Similarly, if the sampled input signal is lower than the reference voltage across capacitor 58, control logic 40 turns on current source 44 and turns off current source 42, thereby discharging capacitor 58. While capacitor 58 is charging or discharging, control logic 40 provides a corresponding directional signal to clock logic 56, which increments the count of counter 60 at the rate of the fast clock by providing count signals to counter 60. When the capacitor 58 is charged to the same voltage as the sampled input signal, the output of comparator 46 reverses, signaling control logic 40 to turn off current supplies 42 and 44 and to turn off input amplifier 48 and comparator 46. Thus, for the remainder of the slow clock cycle, no power is drawn by these components. Control logic 40 also provides a directional signal to clock logic 56. The directional signal provided to clock logic 56 by control logic 40 reverses in response to the reversed output from comparator 46, indicating to clock logic 56 to hold the count of counter 60 constant.

The output of counter 60 is read at output terminal 62 just prior to being reset at the next slow clock pulse. At this point, the initial output of comparator 46, which was stored by control logic 40, may be read out as well. This value provides an additional bit of voltage resolution, so that the eight ($2^3=3$ bits) fast clock pulses per slow clock cycle in combination with this bit provide four bits of voltage resolution as in a conventional delta modulator. However, in the delta modulator according to the invention, instead of four bits of amplitude data there are three bits of amplitude data and one bit of directional data. The digital output that is read out is proportional to the relative movement of the input signal with respect to its previous value.

The power savings that are obtained by shutting off input amplifier 48, comparator 46 and current sources 42 and 44 are greatest when the sampled input signal is constant, as occurs for substantial portions of an intracardial signal. In this case, comparator 46 reverses within a few of the fast clock pulses and the current sources are shut down for most of the slow clock cycle. In contrast, when conventional delta modulators have a constant input the capacitor is continually charged and discharged as the count of the up-down counter oscillates up and down by a single count.

In addition to saving power by turning off the comparator, the input amplifier, and the current sources after a sample has been digitized, power consumption in the delta modulator of the present invention is lowered by using a reduced clock rate of four KHz. Further, the lower clock rate allows the comparator to have a slower frequency response than was previously required, which again permits this component to be more compact and draw less current. While the delta modulator of the present invention has the same voltage resolution as conventional delta modulators, power consumption is reduced to one sixteenth of the previous level when the input signal to be digitized is constant.

Figure 3:
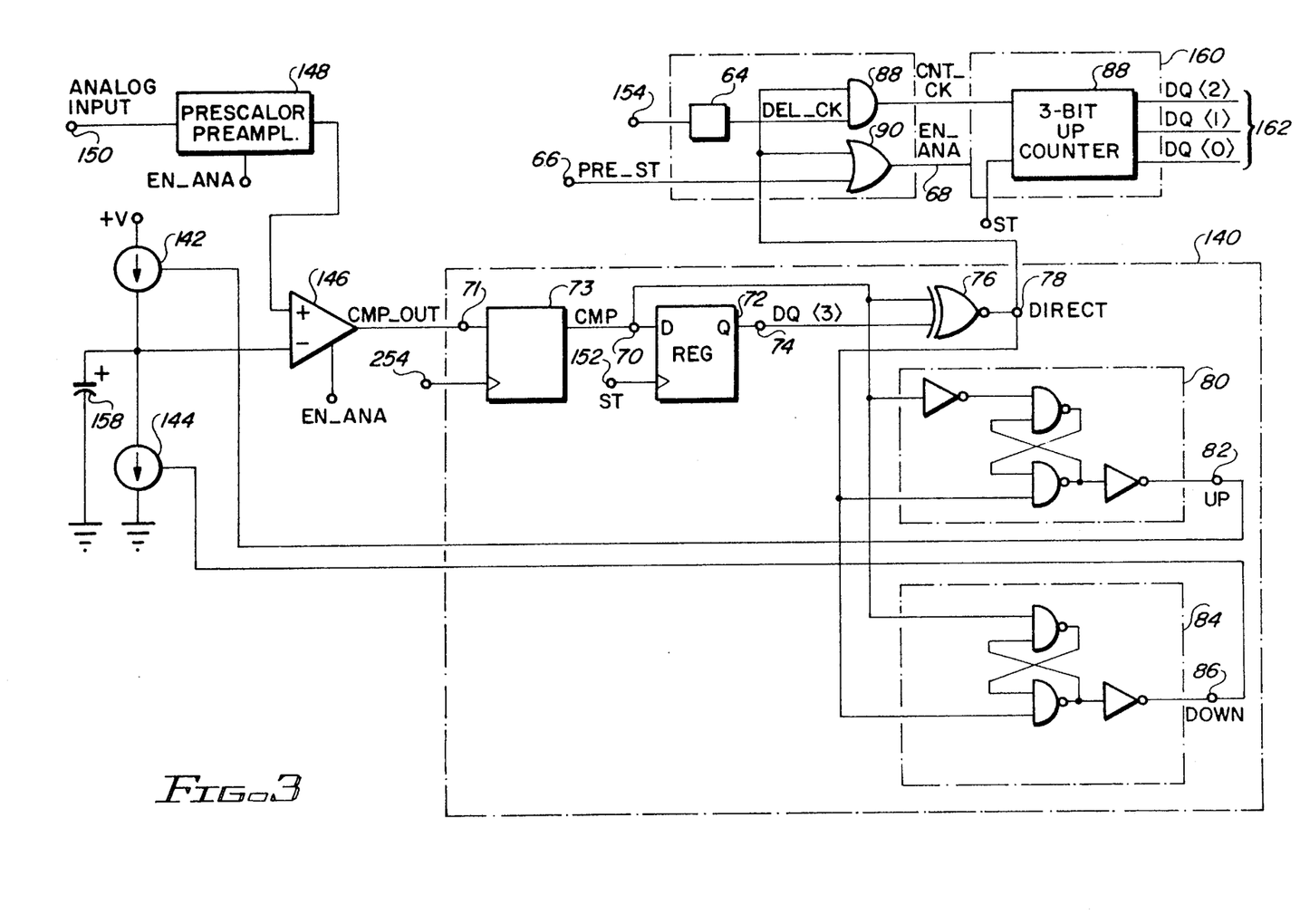
FIG. 3 is a circuit diagram of a preferred illustrative embodiment of a low-power delta modulator in accordance with the present invention.
Figure 4:
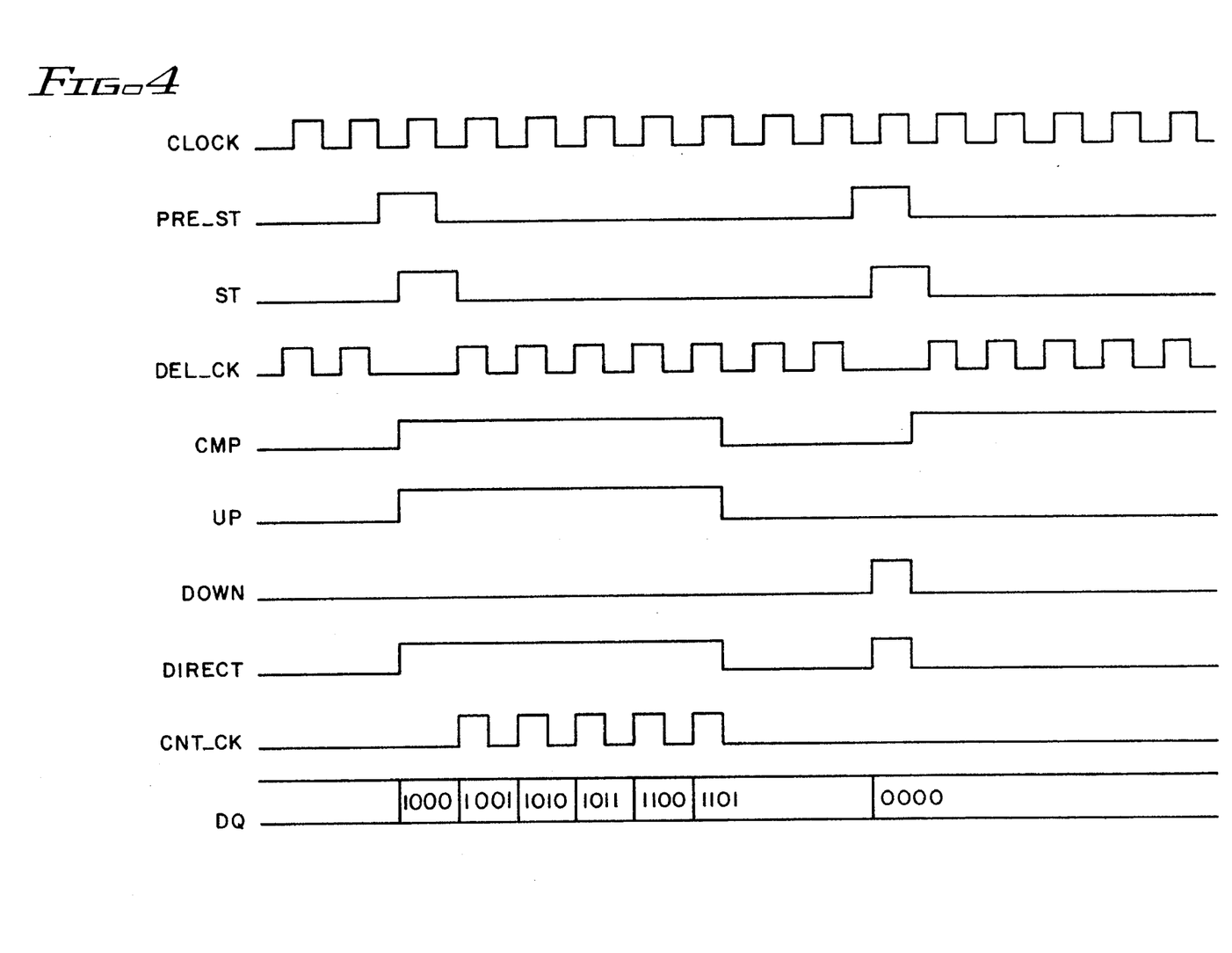
FIG. 4 is a detailed timing diagram of one conversion cycle for the signals of the embodiment of FIG. 3.
Figure 5:
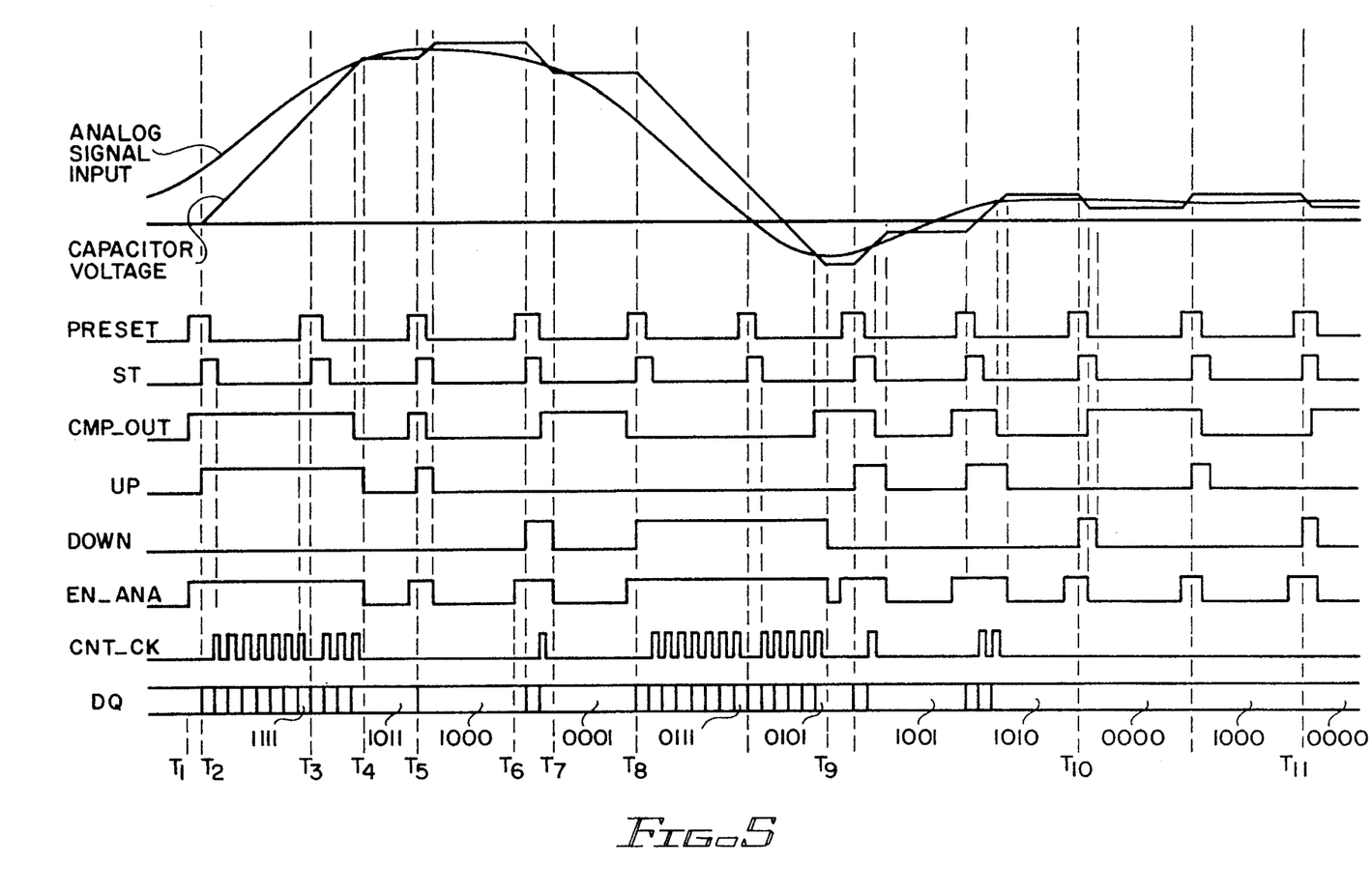
FIG. 5 is a timing diagram of several conversion cycles for the signals of the embodiment of FIG. 3.

A preferred illustrative embodiment of the low-power delta modulator of the present invention and timing diagrams for this embodiment are shown in FIGS. 3, 4, and 5. A clock signal with a frequency of preferably four KHz is applied to terminal 154 of gating logic 64 where it is combined with the signal PRE_ST, using any of several possible conventional approaches, to form the gated clock signal DEL_CK. The PRE_ST clock signal, which is applied to slow clock terminal 66, is advanced by one half of the four KHz clock period with respect to the ST signal, which is applied to slow clock terminal 152. This offset allows the EN_ANA signal produced at terminal 68 of clock logic 156 to enable input logic 148 and comparator 146, just prior to the beginning of an ST cycle. Once enabled, input logic 148 captures an input signal, such as an intracardial signal, that is applied at input terminal 150. Comparator 146, which has been enabled, compares the sampled input signal that is provided by input logic 148 to the reference voltage across capacitor 158, and provides the resulting CMP_OUT signal to data input terminal 71 of flip-flop 73. Flip-flop 73 is clocked by the four KHz clock at terminal 254. The output signal of flip-flop 73, CMP, is provided to the data input terminal 70 of flip-flop 72. Flip-flop 72 is clocked by the ST signal. The ST signal is derived from the fast four KHz clock using any of several possible conventional approaches. The logic required to generate the ST signal induces a small delay of a few nanoseconds, allowing the CMP output signal of flip-flop 73 to be valid prior to flip-flop 72 being clocked.

If the input signal is greater than the reference voltage across capacitor 158, the resulting high CMP signal will be clocked to output terminal 74 of flip-flop 72 when the ST signal goes high. The output signal DQ(3) at output terminal 74, which is the leading bit of the four-bit digital output, is provided with the CMP signal to the inputs of exclusive NOR gate 76. Thus, when ST has risen, the inputs to exclusive NOR gate 76 are both high, and the resulting DIRECT signal at output terminal 78 goes high.

When the DIRECT signal becomes high, up logic 80 of control logic 140 produces a high UP control signal at output terminal 82 and down logic 84 produces a low DOWN control signal at output terminal 86. The high UP and low DOWN control signals turn current source 142 on and current source 144 off, respectively, thus charging capacitor 158. The high DIRECT signal is simultaneously applied to AND gate 88, which provides the CNT_CK signal to counter 160. On the rising edge of the ST signal counter 160 is reset, so that when the CNT_CK signal is received, counter 160 counts the CNT_CK pulses. Counter 160 is preferably a unidirectional counter, such as a three-bit up counter.

After capacitor 158 has been charged sufficiently to balance the sampled input signal, the CMP_OUT output signal of comparator 146 goes low. The next CLOCK rising edge will cause the CMP signal from flip-flop 73 to go low, while the DQ(3) signal that was stored in flip-flop 72 remains high at output terminal 74 of flip-flop 72. As a result, the DIRECT output signal of exclusive NOR gate 76 goes low, causing the UP control signal at output terminal 82 of up logic 80 to go low. The low UP control signal turns off current source 142 for the remainder of the ST cycle. The low DIRECT signal also prevents the DOWN signal from going high, as would be the case with conventional delta modulators. Current sources 142 and 144 thus remain off for the remainder of the cycle. Further, when the DIRECT signal goes low the EN_ANA signal at output terminal 68 goes low because the PRE_ST signal applied to OR gate 90 is also low. This disables input logic 148 and comparator 146 and thereby saves additional power that would have been drawn by these components.

With the DIRECT signal low, the CNT_CK signal at the output of AND gate 88 goes low and counter 160 is held fixed at the count reached when comparator 146 reversed. The value of the lower three bits of the DQ signal at output 162 and the DQ(3) value may be read out just prior to the beginning of the next ST cycle, for instance, when the PRE_ST signal next goes high. The DQ(3) bit represents the initial direction in which the capacitor was to be charged, and is provided at output terminal 74 of flip-flop 72. The circuitry operates similarly when there is initially a higher reference voltage across capacitor 158 than has been sampled by input logic 148. The CMP signal from flip-flop 73 will be low while the DIRECT signal is high. This will cause up logic 80 to generate a low UP signal, and down logic 84 to generate a high DOWN signal. In this case current source 142 will remain off and current source 144 will be turned on. Counter 160 will again count upward, but the DQ(3) value that represents the initial output of comparator 146 will be low.

Two conversion cycles are illustrated in FIG. 4. In addition to the signals described above, the DQ signals are shown. The DQ signals are shown following a vertical bar which corresponds to the CLOCK edge at which the DQ signals attain that value. The first conversion cycle begins with the initial rising edge of PRE_ST. When ST rises the CMP, DIRECT, and UP signals all become high indicating that the input signal to the comparator 146 is greater than the reference voltage across capacitor 158. At this time the value of DQ is 1000, as DQ(3) has been set to 1 by flip-flop 72, while the lower three bits of DQ are represented by the count of counter 160, which was reset by ST. The count of counter 160 increases by one for each CLOCK cycle, while the high UP signal turns current source 142 on, thereby charging capacitor 158. This is shown in FIG. 4, where the lowest three bits of the DQ signal successively increase until reaching 101. At the next rising edge of CLOCK, flip-flop 73 receives a logic low (CMP_OUT), which is stored in flip-flop 73. This is because capacitor 158 has been charged until the voltage across it is greater than the input signal to comparator 146. At this time the CMP, DIRECT, and UP signals all go low. Because the DIRECT signal is low, further generation of CNT_CK cycles is blocked, which prevents counter 160 from incrementing. The value of DQ remains 1101 from this point until the next conversion cycle.

In the second conversion cycle illustrated in FIG. 4, the CMP signal is low when the rising edge of ST occurs. This causes the value of DQ(3) stored in flip-flop 72 to be 0. The first rising edge of DEL_CK causes the CMP signal to go high. The high CMP signal indicates that only one CLOCK cycle was required for the current source 144 to reduce the voltage across capacitor 158 to lower than that of the input signal to comparator 146. When CMP goes high, the value of DQ(3) and CMP will be different, causing the DIRECT signal to go low. Since DIRECT is now low, the CNT_CK signal will remain low. Because CNT_CK is low, counter 160 does not count, thus holding the value of DQ at 0000.

A number of additional conversion cycles are shown in FIG. 5. An illustrative analog input signal is shown, along with the corresponding voltage of capacitor 158. At time T1, which is one clock pulse before the ST signal, the system enables the input logic 148 and the comparator 146. At T2, when the ST signal is high, the system determines the direction in which the voltage of capacitor 158 is to be driven. If the CMP_OUT signal is high at T2, then the capacitor will be charged. If the CMP_OUT signal is low at T2, the capacitor will be discharged. From T2 to T3, the current source 142 is on and the current source 144 is off, thereby charging the capacitor 158 with a total of eight "units" of charge. The CMP_OUT signal inverts before T4, causing the EN_ANA signal to be inactive at T4, which causes the input logic 148, the comparator 146, and current sources 142 and 144 to shut down. CNT_CLK also stops at T4. The combination of the counter value (the lower three bits of the DQ signal) and the directional bit, DQ(3) make up the full DQ signal that is used as the digital output of the device.

At T5, the output of the comparator is high, so for this ST cycle the capacitor 158 is charged and the directional bit is high. However, because the CMP_OUT signal falls before the first clock, the DQ signal is "1000."

At T6, the output of the comparator 146 is low, so for this ST cycle the capacitor is discharged and the directional bit is low. Because the output of the comparator 146 was changed before T7, the ENA_ANA signal is inactive.

From T8 to T9, the logic circuitry of the low-power delta modulator operates as described in connection with the operation from T2 to T4, with the exception that the direction of operation of current sources 142 and 144 and the polarity of the corresponding directional bit are reversed.

When the analog input signal at input terminal 150 is changed very slowly, as shown from T10 to T11, the input logic 148, the comparator 146, and the current sources 142 and 144 operate at one eighth of the maximum rate, thereby saving considerable power.

Thus, it is seen that a delta modulator is provided for monitoring intracardial signals that converts an analog input signal to a digital output signal at greatly reduced power consumption compared to a conventional delta modulator, is provided. One skilled in the art will appreciate that the present invention can be produced by other than the described embodiments, which are provided for purposes of illustration and not of limitation, and the present invention is limited only by the claims which follow.

What is claimed is:

1. A low-power delta modulator for use in a cardiac stimulating device for monitoring intracardial signals, the low-power delta modulator comprising:

input logic for sampling an analog input signal and providing a sampled input signal;

means for providing a reference voltage responsive to control signals;

a first clock;

a counter; and control means for providing the control signals to the means for providing a reference voltage, the means for providing a reference voltage adjusting the reference voltage from an initial reference voltage to substantially equal the sampled input signal in accordance with the control signals, wherein while the means for providing a reference voltage adjusts the reference voltage, the control means simultaneously causes the counter to count at the rate of the first clock until the reference voltage has been adjusted to substantially equal the sampled input voltage, such that a count is reached that is proportional to the voltage difference between the initial reference voltage and the sampled input signal, the control means further providing a directional signal that is indicative of the direction in which the reference voltage was adjusted, and the directional signal and the count being provided as a digital output signal representative of the analog input signal.

2. The delta modulator of claim 1, wherein the control means comprises:

a comparator connected to the input logic and to the means for providing a reference voltage for comparing the sampled input signal to the reference voltage and providing a comparator output accordingly;

a second clock slower than the first clock;

control logic clocked by the first clock for receiving the comparator output, the control logic providing the control signals to the means for providing the reference voltage and providing the directional signal accordingly; and clock logic clocked by the second clock and by the first clock, the clock logic receiving the directional signal from the control logic and providing count signals representative of the voltage difference between the initial reference voltage and the sampled input signal to the counter, such that the counter counts to and stops at the count that is proportional to the voltage difference between the initial reference voltage and the sampled input signal.

3. The delta modulator of claim 2, wherein the means for providing a reference voltage comprises:

a capacitor connected to the comparator, such that the comparator measures the reference voltage across the capacitor; and first and second current sources connected to the capacitor, wherein the capacitor charges when the first current source is on and the second current source is off in accordance with the control signals received from the control logic when the sampled input signal is greater than the reference voltage, and the capacitor discharges when the first current source is off and the second current source is on in accordance with the control signals received from the control logic when the sampled input signal is less than the reference voltage.

4. The delta modulator of claim 3, wherein the control logic further comprises:

up logic connected to the first current source for turning on the first current source when the control signals indicate that the sampled input voltage is greater than the reference voltage and for turning off the first current source when the control signals indicate that the sampled input voltage is less than the reference voltage; and down logic connected to the second current source for turning off the second current source when the control signals indicate that the sampled input signal is greater than the reference voltage and for turning on the second current source when the control signals indicate that the sampled input signal is less than the reference voltage.

5. The delta modulator of claim 4, wherein the control logic further comprises a flip-flop for receiving the comparator output, wherein the flip-flop is clocked by the second clock so that following a pulse of the second clock, the flip-flop has stored the initial value of the comparator output and provides a corresponding flip-flop output.

6. The delta modulator of claim 5, wherein the control logic further comprises an exclusive-NOR gate for receiving the comparator output and the flip-flop output and for providing the directional signal to the clock logic and the up and down logic accordingly.

7. The delta modulator of claim 5, wherein:

the counter is unidirectional; and an additional bit of the digital output that is representative of the directional signal is obtained from the flip-flop output.

8. The delta modulator of claim 2, wherein the clock logic, further comprises:

enabling means for enabling the comparator and the input logic, the enabling means receiving the directional signal and an advanced clock signal that is advanced with respect to the second clock, the enabling means providing an enabling signal to the comparator and the input logic such that the comparator and the input logic are enabled from when the advanced clock signal rises to when the directional signal reverses.

9. The delta modulator of claim 8, wherein the enabling means comprises an OR gate that receives the advanced clock signal and the directional signal and provides the enabling signal accordingly.

10. The delta modulator of claim 8, wherein the clock logic, further comprises:

gating logic for receiving the advanced clock signal and the first clock, the gating logic providing a gated clock signal; and an AND gate for receiving the gated clock signal and the directional signal and providing the count signals accordingly.

11. A low-power delta modulator for use in a cardiac stimulating device for monitoring intracardial signals and converting an analog input signal to a digital output signal, said low-power delta modulator comprising:

a first clock;

a second clock slower than the first clock;

input logic for sampling the analog input signal and providing a sampled input signal;

a capacitor;

a first current source connected to the capacitor;

a second current source connected to the capacitor, the capacitor charging when the first current source is on and the second current source is off in accordance with control signals when the sampled input signal is greater than an initial reference voltage measured across the capacitor, and the capacitor discharging when the first current source is off and the second current source is on in accordance with control signals when the sampled input signal is less than the initial reference voltage;

a comparator connected to the input logic and to the capacitor for comparing the sampled input signal to the reference voltage and providing a comparator output accordingly;

control logic clocked by the second clock for receiving the comparator output, the control logic providing the control signals to the first and second current sources accordingly and providing a directional signal representative of direction of the sampled input signal with respect to the reference voltage;

clock logic clocked by the second clock and by the first clock, the clock logic receiving the directional signal from the control logic and providing corresponding count signals representative of a voltage difference between the sampled input signal and the reference voltage; and a counter for receiving the count signals from the clock logic and for counting to and stopping at a count that is proportional to the voltage difference between the sampled input signal and the reference voltage as represented by the count signals, the counter providing the digital output signal in accordance with the count.

12. The delta modulator of claim 11, wherein the means for providing a reference voltage comprises:

a capacitor connected to the comparator, such that the comparator measures the reference voltage across the capacitor; and first and second current sources connected to the capacitor, wherein the capacitor charges when the first current source is on and the second current source is off in accordance with the control signals received from the control logic when the sampled input signal is greater than the reference voltage, and the capacitor discharges when the first current source is off and the second current source is on in accordance with the control signals received from the control logic when the sampled input signal is less than the reference voltage.

13. The delta modulator of claim 12, wherein the control logic, further comprises a flip-flop for receiving the comparator output, wherein the flip-flop is clocked by the second clock so that following a pulse of the second clock, the flip-flop has stored the initial value of the comparator output and provides a corresponding flip-flop output.

14. The delta modulator of claim 13, wherein the control logic further comprises an exclusive-NOR gate for receiving the comparator output and the flip-flop output and for providing the directional signal to the clock logic and the up and down logic accordingly.

15. The delta modulator of claim 14, wherein:

the counter is unidirectional; and an additional bit of the digital output that is representative of the directional signal is obtained from the flip-flop output.

16. The delta modulator of claim 15, wherein the clock logic, further comprises:

enabling means for enabling the comparator and the input logic, the enabling means receiving the directional signal and an advanced clock signal that is advanced with respect to the second clock, the enabling means providing an enabling signal to the comparator and the input logic such that the comparator and the input logic are enabled from when the advanced clock signal rises to when the directional signal reverses.

17. The delta modulator of claim 16, wherein the enabling means comprises an OR gate that receives the advanced clock signal and the directional signal and provides the enabling signal accordingly.

18. The delta modulator of claim 17, wherein the clock logic, further comprises:

gating logic for receiving the advanced clock signal and the first clock, the gating logic providing a gated clock signal; and an AND gate for receiving the gated clock signal and the directional signal and providing the count signals accordingly.

19. A cardiac stimulating device having a low-power delta modulator for monitoring intracardial signals, the low-power delta modulator comprising:

input logic for sampling an analog input signal and providing a sampled input signal;

means for providing a reference voltage responsive to control signals;

a first clock;

a counter; and control means for providing the control signals to the means for providing a reference voltage, the means for providing a reference voltage adjusting the reference voltage from an initial reference voltage to substantially equal the sampled input signal in accordance with the control signals, wherein while the means for providing a reference voltage adjusts the reference voltage, the control means simultaneously causes the counter to count at the rate of the first clock until the reference voltage has been adjusted to substantially equal the sampled input voltage, such that a count is reached that is proportional to the voltage difference between the initial reference voltage and the sampled input signal, the control means further providing a directional signal that is indicative of the direction in which the reference voltage was adjusted, and the directional signal and the count being provided as a digital output signal representative of the analog input signal.

20. The cardiac stimulating device of claim 19, wherein the control means comprises:

a comparator connected to the input logic and to the means for providing a reference voltage for comparing the sampled input signal to the reference voltage and providing a comparator output accordingly;

a second clock slower than the first clock;

control logic clocked by the first clock for receiving the comparator output, the control logic providing the control signals to the means for providing the reference voltage and providing the directional signal accordingly; and clock logic clocked by the second clock and by the first clock, the clock logic receiving the directional signal from the control logic and providing count signals representative of the voltage difference between the initial reference voltage and the sampled input signal to the counter, such that the counter counts to and stops at the count that is proportional to the voltage difference between the initial reference voltage and the sampled input signal.

21. The cardiac stimulating device of claim 20, wherein the means for providing a reference voltage comprises:

a capacitor connected to the comparator, such that the comparator measures the reference voltage across the capacitor; and first and second current sources connected to the capacitor, wherein the capacitor charges when the first current source is on and the second current source is off in accordance with the control signals received from the control logic when the sampled input signal is greater than the reference voltage, and the capacitor discharges when the first current source is off and the second current source is on in accordance with the control signals received from the control logic when the sampled input signal is less than the reference voltage.

22. The cardiac stimulating device of claim 21, wherein the control logic further comprises:

up logic connected to the first current source for turning on the first current source when the control signals indicate that the sampled input voltage is greater than the reference voltage and the up logic turns off the first current source when the control signals indicate that the sampled input voltage in less than the reference voltage; and down logic connected to the second current source for turning off the second current source when the control signals indicate that the sampled input signal is greater than the reference voltage and the down logic turns on the second current source when the control signals indicate that the sampled input signal is less than the reference voltage.

23. The cardiac stimulating device of claim 22, wherein the control logic further comprises a flip-flop for receiving the comparator output, wherein the flip-flop is clocked by the slow clock, so that following a slow clock pulse, the flip-flop has stored the initial value of the comparator output and provides a corresponding flip-flop output.

24. The cardiac stimulating device of claim 23, wherein the control logic further comprises an exclusive NOR gate for receiving the comparator output and the flip-flop output, and for providing the directional signal to the clock logic and the up and down logic accordingly.

25. The cardiac stimulating device of claim 23, wherein:

the counter is unidirectional; and an additional bit of the digital output that is representative of the directional signal is obtained from the flip-flop output.

26. The cardiac stimulating device of claim 20, wherein the clock logic, further comprises:

enabling means for enabling the comparator and the input logic, the enabling means receiving the directional signal and an advanced clock signal that is advanced with respect to the second clock, the enabling means providing an enabling signal to the comparator and the input logic such that the comparator and the input logic are enabled from when the advanced clock signal rises to when the directional signal reverses.

27. The cardiac stimulating device of claim 26, wherein the enabling means comprises an OR gate that receives the advanced clock signal and the directional signal and provides the enabling signal accordingly.

28. The cardiac stimulating device of claim 26, wherein the clock logic, further comprises:

gating logic for receiving the advanced clock signal and the first clock, the gating logic providing a gated clock signal; and an AND gate for receiving the gated clock signal and the directional signal and providing the count signals accordingly.

29. A method for monitoring intracardial signals with a low-power delta modulator in a cardiac stimulating device, comprising the steps of:

sampling an analog input signal with input logic to provide a sampled input signal;

providing a reference voltage that may be adjusted in response to control signals until the reference voltage is substantially equal to the sampled input signal;

causing a counter to count while the reference voltage is adjusted, the counter counting at the rate of a first clock until the reference voltage has been adjusted to substantially equal the sampled input signal, such that the count that is reached is proportional to the voltage difference between an initial reference voltage and the sampled input signal;

providing a directional signal that is indicative of the direction in which the reference voltage was adjusted; and providing the directional signal and the count as a digital output signal representative of the analog input signal.

30. The method of claim 29, further comprising the steps of:

comparing the sampled input signal to the reference voltage using a comparator;

providing a corresponding comparator output to control logic;

clocking the control logic with a second clock that is slower than the first clock;

receiving the comparator output with the control logic;

providing the control signals using the control logic so that the reference voltage is raised and lowered in accordance with the comparator output;

providing the directional signal using the control logic;

clocking clock logic with the second clock and the first clock;

receiving into the clock logic the directional signal from the control logic;

providing corresponding count signals using the clock logic;

receiving the count signals from the clock logic into the counter; and counting to and stopping at the count that is proportional to the difference between the initial reference voltage and the sampled input signal in accordance with the count signals.

31. The method of claim 30, wherein the step of providing a reference voltage comprises the steps of:

measuring the reference voltage across a capacitor that is connected to the comparator;

charging the capacitor with a first current source that is connected to the comparator when the first current source is on and a second current source is off in accordance with control signals received from the control logic; and discharging the capacitor with the second current source that is connected to the capacitor when the first current source is off and the second current source is on in accordance with control signals received from the control logic.

32. The method of claim 31, wherein the steps of charging and discharging the capacitor, further comprise the steps of:

providing the control signals to the first current source in accordance with the comparator output using up logic connected to the first current source; and providing the control signals to the second current source in accordance with the comparator output using down logic connected to the second current source.

33. The method of claim 30, wherein the step of receiving the comparator output, further comprises the step of clocking the comparator output into a flip-flop with the second clock, so that following a clock pulse from the second clock, the flip-flop has stored the initial value of the comparator output and provides a corresponding flip-flop output.

34. The method of claim 33, further comprising the steps of:

receiving the comparator output and the flip-flop output with an exclusive NOR gate; and providing the directional signal to the clock logic and the up and down logic accordingly.

35. The method of claim 33, further comprising the steps of:

obtaining an additional bit of the digital output from the flip-flop output; and providing the remainder of the digital output from the output of the counter, wherein the counter is unidirectional.

36. The method of claim 33, further comprising the steps of:

receiving the directional signal;

receiving an advanced clock signal that is advanced with respect to the second clock; and providing an enabling signal to the comparator and the input logic such that the comparator and the input logic are enabled from when the advanced clock signal rises to when the directional signal reverses.

37. The method of claim 36, wherein the steps of receiving the advanced clock signal and the directional signal, further comprise the steps of:

receiving the advanced clock signal with an OR gate;

receiving the directional signal with the OR gate; and providing the enabling signal accordingly.

38. The method of claim 36, wherein the step of providing count signals, further comprises the steps of:

receiving the advanced clock signal with gating logic;

receiving the first clock with the gating logic;

providing a gated clock signal accordingly;

receiving the gated clock signal with an AND gate;

receiving the directional signal with the AND gate; and providing the count signals accordingly.

* * * * *